United States Patent [19]

Moore, Jr. et al.

[11] Patent Number: 5,141,652

[45] Date of Patent: Aug. 25, 1992

[54] WATER TREATMENT PROCESS

[75] Inventors: Robert M. Moore, Jr., Baton Rouge, La.; Clarinda M. Whitton, Collinsville, Ill.; Lawrence H. Shepherd, Jr., Baton Rouge, La.

[73] Assignee: Ethyl Corporation, Richmond, Va.

[21] Appl. No.: 714,211

[22] Filed: Jun. 12, 1991

Related U.S. Application Data

[63] Continuation-in-part of Ser. No. 510,589, Apr. 18, 1990, abandoned.

[51] Int. Cl.$^5$ .............................................. C02F 1/76
[52] U.S. Cl. .................................... 210/754; 210/764; 424/663; 424/723
[58] Field of Search ....................... 210/753, 754, 764; 423/466; 424/663, 665, 723

[56] References Cited

U.S. PATENT DOCUMENTS

| | | | |
|---|---|---|---|
| 2,662,855 | 12/1953 | Kamlet | 210/28 |
| 4,144,211 | 3/1979 | Chamberlin et al. | 260/29 |
| 4,186,191 | 1/1980 | Chamberlin et al. | 424/78 |
| 4,408,001 | 10/1983 | Ginter et al. | 524/376 |
| 4,411,799 | 10/1983 | Ito et al. | 210/753 |
| 4,594,392 | 6/1986 | Hatch | 525/327 |
| 4,614,595 | 9/1986 | Azzarella et al. | 210/754 |
| 4,759,852 | 7/1988 | Trulear | 210/699 |
| 4,770,198 | 9/1988 | Bergman | 137/1 |
| 4,822,513 | 4/1989 | Corby | 252/106 |
| 4,846,979 | 7/1989 | Hamilton | 210/754 |
| 4,872,999 | 10/1989 | Schild et al. | 210/754 |
| 4,883,600 | 11/1989 | MacDonald et al. | 210/696 |

FOREIGN PATENT DOCUMENTS 0184904 10/1986 European Pat. Off.

OTHER PUBLICATIONS

Chemical Abstract 105(2):11746k.
Chemical Abstract 98 (8):59661t.
Chemical Abstract 93 (20):191625k.
Chemical Abstract 89 (20):168858x.
Chemical Abstract 87(24):189197e.
Chemical Abstract 83(2):15170t.
Chemical Abstract 100(4):25893q.
Chemical Abstract 89(11):85502a.
Chemical Abstract 87(4):28797k.
Anderson, A. C., *American Journal of Public Health*, vol. 72, No. 11 pp. 1290–1293 (1982) (abstract only).
Burton, D. T. et al, Bulletin of Environmental Contamination and Toxicology, vol. 19, No. 2, pp. 131–138 (1978) (abstract only).
Butler, M. et al, *Water Science and Technology*, vol. 17, No. 10, pp. 201–210 (1985) (abstract only).
Chiesa, Robert et al, *Annual Meeting—International Water Conference 46th*, pp. 414–426 (1985) (abstract only).
Cotruvo, J. A., Water Chlorination: Environmental Impact and Helath Effects, vol. 4, No. 2, pp. 1417–1422 (1983) (abstract only).
Grover, K., *American City and County* 95(9) pp. 67–68 (1980) (abstract only).
Haas, C. N. et al, Jounral of the Water Pollution Control Federation, 54(6) pp. 646–654 (1982) (abstract only).
Jones, Blair, *Water/Engineering and Management*, 135(3), pp. 34–35 (1988) (abstract only).
Keswick, B. H. et al., "Bromine Chloride: An Alternative Disinfectant to Chlorine", No. 54 (1977) (abstract only).
Keswick, B. H. et al, Journal of the American Water Works Assocation, 70 (10) pp. 573–577 (1978) (abstract only).
Keswick, B. H. et al, Journal Water Pollution Control Federation 52 (10) pp. 2581–2588 (1980) (abstract only).
Keswick, B. H. et al, Water Research 16 (1) pp. 89–94 (1982) (abstract only).
Kopperman, H. L. et al, *Proceedings of the Conference on the Environmental Impact of Water Chlorination*, Oct. 22–24, pp. 327–345 (1975) (abstract only).
Leblanc, N. E. et al, *Water Chlorination: Environmental Impact and Health Effects* vol. 2, pp. 637–650 (1978) (abstract only).
Lau, L. S. et al, "Recycling of Sewerage Effluent by Sugarcane Irrigation: A Posttreatment Study" (1977) (abstract only).
Mills, J. F., Am. Chem. Soc., Div. Water, Air Waste Chem., Gen. Pap. 13(1) p. 106 (1973) (abstract only).
Mills, "Interhalogens and Halogen Mixtures as Disinfectants," Disinfection–Water and Wastewater (1975) pp. 113–143.
Mills, Jack F., *Proc. of Mid-Atlantic Ind Waste Conf*, 9th, pp. 203–206 (1977) (abstract only).
Mills, J. F., The Chemistry of Bromine Chloride in Waste Water Disinfection in Preprint of Papers Presented at 166th National Meeting of American Chemical Society, Aug. 1973, Chicago, Ill: American Chemical Society Division of Environmental Chemistry, 13(2) pp.1 37–143 (1973) (abstract only).
Randle, R. W., "Effects of Bromine Chloride on Several Unicellular Green Algal Species Under Laboratory Conditions" (1978) (abstract only).
Rice, R. G., *Water Pollution Control*, 77(1), pp. 51–55 (1978) (abstract only).
Smith, J. W., Water and Wastes Engineering, 15(6), pp. 18–25 (1978) (abstract only).
Taylor, D. G. et al, *Am. Chem. Soc., Div. Water, Air Waste Chem.*, Gen Pap. 13(1) pp. 103–104 (1973) (abstract only).
Tonelli, F. A. et al, Proceedings of the Seminar on Current Approaches in Wasterwater Treatment, pp. 117–138 (1978).
Venosa, A. D. et al, Water Chlorination: Environmental Impact and Health Effects vol. 2, pp. 625–628 (1978) (abstract only).
Ward, R. W. et al, "Disinfection Efficiency and Residual Toxicity of Several Wastewater Disinfectants: Vol. I" (1976) (abstract only).
Ward, R. W. et al, *J. Water Pollut. Control Fed.* 50(10) pp. 46–60 (1978) (abstract only).
Ward, R. W. et al, *Water Resources Bulletin* 14(3) pp. 696–709 (1978) (abstract only).

Winklehaus, C., *Jounal Water Pollution Control Federation*, 49(2) pp. 190-193 (1977) (abstract only).
Winklehaus, C., *Jounral Water Pollution Control Federation*, 49(12) pp. 2354-2357 (1977) (abstract only).
Zeh, T. C. Jr., *Public Works*, 115(10) pp. 56-57 (1984) (abstract only).
*The American City and Country*, vol. 93, No. 3, pp. 82-83 (1978) (abstract only).
*Chem. Engr. News*, Oct. 10, (1978) (abstract only).
"Disinfection of Wastewater, Task Force Report", Mar., 1976 (abstract only).
*Dow Bromine Chloride Handbook* (Publication date unkown).
Ethyl Corporation "Bromide Chloride for Treating Cooling Water and Waste Water" Bulletin BC-4 [984], published approx. 1984.
Water Chlorination: Environmental Impact and Health Effects 4(2) (1983) (abstract only).

*Primary Examiner*—Peter Hruskoci
*Attorney, Agent, or Firm*—David E. LaRose

[57] ABSTRACT

This invention relates to a process for reducing the biological activity in water by feeding a solution of BrCl stabilized by a hydrohalic acid or an aqueous halide salt into the water to be treated in an amount sufficient to effect the reduction of biological activity in the water thus treated.

38 Claims, No Drawings

WATER TREATMENT PROCESS

This is a continuation-in-part of application Ser. No. 07/510,589, filed Apr. 18, 1990 now abandoned.

FIELD

This invention relates to a process for the treatment of water for the purpose of reducing biological activity therein.

BACKGROUND

Chlorine ($Cl_2$), bromine ($Br)_2$, and bromine chloride (BrCl) are well known in the water treatment industry as effective biocides. At the present time, chlorine, bromine and chloride or bromide-containing molecules capable of undergoing hydrolysis to produce hypohalous acid are the choices of most commercial practitioners of water treatment. These choices however, are not without some serious drawbacks.

Chlorine, which is the most popular choice as a biocide, is disadvantaged as it can form long-lived toxic chloramines with ammonia, which could very well be present in the water to be treated. Laboratory studies have indicated that chloramines in concentrations as low as 0.1 parts per million (ppm) can produce fish kills. Also when using chlorine in water treatment, the production of hypochlorous acid (HOCl) can lead to the formation of other chlorinated nitrogen-containing compounds which can persist to cause environmental damage should the treated water be released into the environment.

Bromine, though not always the biocide of choice, has advantages over chlorine. Hypobromous acid (HOBr) and bromamines are known to be very effective bactericides and viricides. Furthermore, disinfection of the water using selected bromine-containing species can often be achieved with lower residual levels of bromamine and HOBr than with chlorination. Bromamines also decompose very rapidly, hence their discharge levels in water treated with bromine are very low, even in once-through cooling applications.

When dissolved in a large quantity of water, essentially all of the bromine in BrCl forms hypobromous acid (HOBr) as compared to about one-half of the bromine present when elemental $Br_2$ is used. These and other advantages of bromine chloride are illustrated in Kamlet U.S. Pat. No. 2,662,855 which is incorporated herein by reference.

At the present time, commercial use of BrCl is thwarted by practical considerations. If neat BrCl is used to treat water, there are significant handling problems to overcome. If the BrCl is dissolved in water to overcome such handling problems, the resultant solution is not suitable for long-term use as the hypobromous acid formed therein will soon decompose. Also the amount of BrCl which can be solubilized in water is relatively small, i.e. only about 8.5 grams of BrCl per 100 grams of water at 20° C.

THE INVENTION

This invention relates to a process for reducing the biological activity in a water system in a facile and economically acceptable way. The process comprises: providing a supply of a biocidal solution for use in water treatment, the solution comprising bromine chloride (BrCl), water, and a sufficient amount of a stabilizer comprising a halide salt or hydrohalic acid or a mixture of halide salt and hydrohalic acid such that less than 30% of the BrCl in the biocidal solution reacts with the water per year to form hypobromous acid and hydrochloric acid; and adding from the supply, the biocidal solution to the water system at a rate sufficient to maintain at least 1 to 2 parts of hypobromous acid per million parts of water in the water system.

For the purposes of this invention, the reduction in biological activity means the killing and/or the prevention or reduction in the propagation of living organisms, such as fungi, algae, viruses, bacteria, slimes, protozoa, and accretion forming organisms, found in a water system. Water system can mean any of a number of water and/or water related utilities, including boiler feed water, cooling water, chilled water, waste water, drinking water, swimming pool water, general process water, and the like.

The halide salt substituent used as a stabilizer in the above defined biocidal solution comprises a chloride or bromide anion and an alkali metal, an alkaline-earth metal, a transition metal, or a quaternary ammonium cation. Preferably, the halide salt is $CaBr_2$, $CaCl_2$, KBr, KCl, LiBr, LiCl, $MgCl_2$, $MgBr_2$, NaCl, NaBr, or mixtures of any two or more of the foregoing. In a preferred embodiment, the halide salt is NaCl, KCl, or a mixture thereof, with NaCl being the most preferred.

The hydrohalic acid substituent used as a stabilizer alone or in a mixture with the halide salt is hydrochloric acid, hydrobromic acid, or mixtures thereof. Of the hydrohalic acids, hydrochloric acid is the most preferred.

The amount of stabilizer acid used in the biocidal solution is generally that amount sufficient to provide from about 1 to about 4 moles of halogen anion per liter of solution. The amount of stabilizer used will directly determine the ability of the solution to provide the degree of stability sought. Since many factors are involved, an empirical approach is used. For example, when the stabilizer is NaCl, the process of this invention can be well served by a 0.5 to about 4 molar NaCl concentration and preferably with about a 2.0 to about a 4 molar NaCl solution.

It is preferred that the biocidal solutions of this invention initially contain as much BrCl as will go into solution. This amount of BrCl in the solution will be dependent upon the concentration of the stabilizer and upon the temperature of the solution at the time of solubilization of the BrCl. Generally, when the biocidal solution contains from about a 2 to about a 4 molar concentration of stabilizer, the solution can contain up to a 4 molar concentration of BrCl at 25° C. A lower concentration of stabilizer will result in a lower BrCl concentration. Stabilizer concentrations significantly in excess of the upper end of the above range will not generally add much to an increase of BrCl in the solution. Most preferably, the biocidal solutions of this invention contain about 0.5 to about 2 moles of BrCl per liter of solution.

In forming the biocide solutions of this invention, any conventional technique may be used. Hence, to achieve the desired concentration of BrCl in the aqueous solution of water and the stabilizer, BrCl may be sparged into the aqueous solution as a gas or admixed with the aqueous solution as a liquid. When added to the aqueous solution as a gas, the BrCl is usually sparged into an agitated pressure vessel containing the aqueous solution. By controlling the temperature and pressure within the pressure vessel while vigorously agitating the aqueous solution, the desired amount of BrCl can be dissolved in the aqueous solution.

When the BrCl is added as a liquid to the aqueous solution of water and the stabilizer, its temperature should be within the range of from about −60° C. to about −10° C. and most preferably within the range of from about −60° C. to about −50° C. While the above temperature ranges are typical, other temperatures may be used with the realization that BrCl is in the gaseous state above about −5° C. at atmospheric pressure. While at superatmospheric pressures, BrCl can be added as a liquid even at temperatures above −5° C.

In accordance with the process of this invention, the biocidal solution is added to the water or water system to be treated in an amount and at a rate which will provide the reduction in the biological activity sought. The biocidal solution of this invention is characterized in that it contains a relatively high concentration of BrCl in a stabilizing environment. Thus, it is a feature of the process of this invention that a supply of solution can be located near the water system to be treated and that this supply can provide biocidal effects over a long period of time. Generally, a slow feed from the supply of biocidal solution to the water system will be the method of introducing BrCl. The feed rate should be sufficient to provide at least about 1 to about 2 parts hypobromous acid per million parts of the water being treated. While continuous feed of the biocidal solution may be the general practice, intermittent feed of the biocidal solution may be used if desired. As pointed out previously, the reduction in the conversion of BrCl to hypobromous acid in the biocidal solution is directly related to the stabilizer concentration. However, when the solution is fed to the water to be treated, there is a significant dilution effect seen by the BrCl-containing biocidal solution. Upon dilution of this solution, the concentration of the stabilizer is lost and the BrCl will immediately start to form hypobromous acid at a conventional water treating rate.

Biocidal solutions of this invention can also contain other conventional additives as long as the additives do not adversely effect the stability or solubility of the BrCl in the solution. Since BrCl is an oxidizing agent, the stabilized BrCl solution is the only active ingredient required, since the BrCl functions as both the source of bromine and the oxidizing agent. Hence the cost of treating water is significantly reduced.

With this process it is now finally possible to easily and economically use BrCl as a biocide in water treatment over a long period of time. Also, the feeding equipment needed is simple in design and construction. The biocidal solution can be injected, poured, dripped, metered, pumped, etc. into the water system to be treated. Thus, the process of this invention fills a long-felt need and enables the practitioner to fully obtain the benefit of using BrCl in treating water.

By way of the following non-limiting examples, preparation of the biocidal solutions of this invention and their use are illustrated.

EXAMPLE 1

Biocidal solutions reported in the following Table A were each prepared by the addition of bromine chloride at a temperature of about −60° C. to an agitated vessel containing water and a stabilizer with the indicated concentration. In order to dissolve the bromine chloride, the solution was stirred for 1–3 hours subsequent to the addition of the bromine chloride. The concentration of bromine chloride in the resulting biocidal solution was determined by a modified arsenite-starch-iodine titration technique. After preparation of the biocidal solutions, the solutions were stored in amber bottles in a lighted lab and the amount of bromine chloride hydrolyzed to hypobromous acid after diluting the solution in water was determined by titration with ferrous ammonium sulfate in the presence of N,N',-diethyl-p-phenylenediamine oxalate (DPD) indicator.

The following biocidal solutions prepared by the before-mentioned technique illustrate the stability of the BrCl/aqueous halide salt solutions.

TABLE A

Stability of Aqueous NaCl/BrCl Solutions

| Sample Number | BrCl Conc. (M/L) | NaCl Conc. (M/L) | Days | Decomposition (%) |
|---|---|---|---|---|
| 1 | 0.32 | 1 | 18 | 10 |
| 2 | 0.32 | 1 | 104 | 14 |
| 3 | 0.88 | 4 | 14 | 6 |
| 4 | 0.88 | 4 | 103 | 12 |
| 5 | 0.19 | 2 | 21 | 7 |
| 6 | 0.19 | 2 | 103 | 12 |
| 7 | 0.67 | 1 | 14 | 11 |
| 8 | 0.67 | 1 | 91 | 19 |
| 9 | 0.68 | 2 | 28 | 4 |
| 10 | 0.68 | 2 | 50 | 6 |
| 11 | 0.97 | 4 | 7 | <1 |
| 12 | 0.97 | 4 | 30 | 3 |
| 13 | 0.97 | 4 | 100 | 7 |
| 14 | 0.97 | 4 | 377 | 27 |

As can be seen from Table A, the samples showed remarkable stability. For example, in Samples 9 and 10 hydrolysis of bromine chloride to hypobromous acid was only about 4% after 28 days and 6% after 50 days.

EXAMPLE 2

To further illustrate the process of this invention, two biocidal solutions, solution A and solution B, were prepared and injected into water, simulating a water system. Solution A was comprised of 1.56 M BrCl in 3 M NaCl and Solution B was comprised of 0.891 M BrCl in 3 M NaCl. After injection, the amount of HOBr in the simulated water system was determined by titration with ferrous ammonium sulfate in the presence of DPD indicator. Table B lists, in tabular form, the amount of residual HOBr, reported as free available chlorine equivalents, after the time indicated.

TABLE B

Residual HOBr as a Function of Time

| Solution | BrCl Conc. (M/L) | NaCl Conc. (M/L) | BrCl Solution (mL) | Water (liters) | HOBr (ppm) | Time (minutes) |
|---|---|---|---|---|---|---|
| A[1] | 1.56 | 3 | 0.1 | 2* | 4.70 | 5 |
|  |  |  |  |  | 4.85 | 15 |
| B[1] | 0.891 | 3 | 0.1 | 2* | 3.15 | 5 |
|  |  |  |  |  | 3.05 | 10 |
|  |  |  |  |  | 3.25 | 15 |
| B[2] | 0.891 | 3 | 1 | 40** | 0.75 | 1 |
|  |  |  |  |  | 0.85 | 3 |
|  |  |  | 1 |  | 1.00 | 5 |
|  |  |  |  |  | 1.05 | 10 |
|  |  |  |  |  | 0.85 | 90 |
| A[2] | 1.56 | 3 | 1 | 40** | 1.10 | 15 |
|  |  |  | 1 |  | 3.2 | 25 |

*Deionized water having 0 ppm residual halogen.
**Tap water having 0.12 ppm residual halogen.
A[1] and B[1] single addition of biocidal solution
A[2] and B[2] two 1 mL additions of biocidal solution to water As can be seen from the foregoing examples, by using the stabilized biocidal solutions of this invention, a residual level of HOBr in the water system to be treated, can be obtained. Various modifications of the invention are possible without departing from the spirit and scope of the invention as set forth in the appended claims.

We claim:

1. A process for reducing biological activity in a water system which process comprises
   a) providing a supply of a biocidal solution, which solution comprises
      (i) bromine chloride (BrCl),
      (ii) water,
      (iii) and a sufficient amount of a stabilizer consisting essentially of a halide salt or a hydrohalic acid or a mixture of halide salt and hydrohalic acid such that less than 30% of the BrCl reacts with water per year to form hypobromous acid and hydrochloric acid; and
   b) adding from said supply, said biocidal solution to the water system at a rate sufficient to maintain at least about 1 to 2 parts of hypobromous acid per million parts of water.

2. The process of claim 1 wherein the halide salt is comprised of a chloride or bromide anion and an alkali metal, an alkaline-earth metal, or a quaternary ammonium cation.

3. The process of claim 2 wherein the halide salt is $CaBr_2$, $CaCl_2$, KBr, KCl, LiBr, LiCl, $MgCl_2$, $MgBr_2$, NaCl, or NaBr.

4. The process of claim 3 wherein the halide salt is NaCl.

5. The process of claim 1 wherein the hydrohalic acid is HCl.

6. The process of claim 1 wherein the biocidal solution contains from about 0.1 to about 3.0 moles of BrCl per liter of solution.

7. The process of claim 6 wherein the biocidal solution contains from about 0.5 to about 2 moles of BrCl per liter of solution.

8. The process of claim 1 wherein the biocidal solution contains a sufficient amount of stabilizer to provide from about to about 4 moles of halogen anion per liter of said solution.

9. A process for reducing the biological activity in water which process comprises introducing into the water a biocidal solution comprising BrCl, water, and an amount of a stabilizer consisting essentially of a halide salt or a hydrohalic acid or a mixture of a halide salt and hydrohalic acid, which amount is sufficient to reduce the conversion of BrCl to HOBr and HCl in the biocidal solution to less than 30% per year.

10. The process of claim 9 wherein the halide salt is comprised of a halide anion and an alkali metal, an alkaline-earth metal, or a quaternary ammonium cation.

11. The process of claim 10 wherein the halide salt is $CaBr_2$, $CaCl_2$, KBr, KCl, LiBr, LiCl, $MgCl_2$, $MgBr_2$, NaCl, or NaBr.

12. The process of claim 11 wherein the halide salt is NaCl.

13. The process of claim 9 wherein the hydrohalic acid is HCl.

14. The process of claim 9 wherein the biocidal solution contains a sufficient amount of stabilizer to provide from about 1 to about 4 moles of halogen anion per liter of solution.

15. The process of claim 9 wherein the biocidal solution contains from about 0.1 to about 3.0 moles of BrCl per liter of solution.

16. The process of claim 15 wherein the biocidal solution contains from about 0.5 to about 2 moles of BrCl per liter of solution.

17. A process for reducing the biological activity in water which process comprises introducing into the water a biocidal solution comprising about 0.5 to about 2 moles per liter of BrCl, water, and an amount of a stabilizer consisting essentially of a halide salt or a hydrohalic acid or a mixture of halide salt and hydrohalic acid which amount is sufficient to reduce the conversion of BrCl to HOBr and HCl in the biocidal solution to less than 30% per year.

18. The process of claim 17 wherein the halide salt is NaCl.

19. The process of claim 18 wherein the biocidal solution contains from about 1 to about 4 moles of NaCl per liter of solution.

20. A process for reducing biological activity in a water system which process comprises
   a) providing a supply of a biocidal solution, which solution comprises
      (i) bromine chloride (BrCl),
      (ii) water,
      (iii) and a sufficient amount of a stabilizer comprising a chloride salt or a hydrochloride acid or a mixture of chloride salt and hydrochloride acid such that less than 30% of the BrCl reacts with water per year to form hypobromous acid and hydrochloric acid; and
   b) adding from said supply, said biocidal solution to the water system at a rate sufficient to maintain at least about 1 to 2 parts of hypobromous acid per million parts of water.

21. The process of claim 20 wherein the chloride salt is comprised of a chloride anion and an alkali metal, an alkaline-earth metal, or a quaternary ammonium cation.

22. The process of claim 21 wherein the chloride salt is $CaCl_2$, KCl, LiCl, $MgCl_2$, or NaCl.

23. The process of claim 22 wherein the chloride salt is NaCl.

24. The process of claim 20 wherein the hydrochloride acid is HCl.

25. The process of claim 20 wherein the biocidal solution contains from about 0.1 to about 3.0 moles of BrCl per liter of solution.

26. The process of claim 25 wherein the biocidal solution contains from about 0.5 to about 2 moles of BrCl per liter of solution.

27. The process of claim 20 wherein the biocidal solution contains a sufficient amount of stabilizer to provide from about 1 to about 4 moles of chloride anion per liter of solution.

28. A process for reducing the biological activity in water which process comprises introducing into the water a biocidal solution comprising BrCl, water, and an amount of a stabilizer comprising a chloride salt or a hydrochloride acid or a mixture of a chloride salt and hydrochloride acid, which amount is sufficient to reduce the conversion of BrCl to HOBr and HCl in the biocidal solution to less than 30% per year.

29. The process of claim 28 wherein the chloride salt is comprised of a chloride anion and an alkali metal, an alkaline-earth metal, or a quaternary ammonium cation.

30. The process of claim 29 wherein the chloride salt is $CaCl_2$, KCl, LiCl, $MgCl_2$, or NaCl.

31. The process of claim 30 wherein the chloride salt is NaCl.

32. The process of claim 28 wherein the hydrochloride acid is HCl.

33. The process of claim 28 wherein the biocidal solution contains a sufficient amount of stabilizer to provide from about 1 to about 4 moles of chloride anion per liter of solution.

34. The process of claim 28 wherein the biocidal solution contains from about 0.1 to about 3.0 moles of BrCl per liter of solution.

35. The process of claim 34 wherein the biocidal solution contains from about 0.5 to about 2 moles of BrCl per liter of solution.

36. A process for reducing the biological activity in water which process comprises introducing into the water a biocidal solution comprising about 0.5 to about 2 moles per liter of BrCl, water, and an amount of a stabilizer comprising a chloride salt or a hydrochloride acid or a mixture of chloride salt and hydrochloride acid which amount is sufficient to reduce the conversion of BrCl to HOBr and HCl in the biocidal solution to less than 30% per year.

37. The process of claim 36 wherein the chloride salt is NaCl.

38. The process of claim 37 wherein the biocidal solution contains from about 1 to about 4 moles of NaCl per liter of solution.

* * * * *

UNITED STATES PATENT AND TRADEMARK OFFICE
CERTIFICATE OF CORRECTION

PATENT NO. : 5,141,652

DATED : AUGUST 25, 1992

INVENTOR(S) : ROBERT M. MOORE, JR., ET.AL

It is certified that error appears in the above-identified patent and that said Letters Patent is hereby corrected as shown below:

On the Title page, item [56], under OTHER PUBLICATIONS, col. 2, line 59

In the references:
    Ward, R. W., et al., J. Water Pollut. Control Fed.,
        change "50(10)"
           to -- 50(1) --.

In the Claims, Column 5, Line 44:
    after "from about" insert -- 1 --.

Signed and Sealed this

Twenty-eighth Day of September, 1993

Attest:

BRUCE LEHMAN

*Attesting Officer*     *Commissioner of Patents and Trademarks*